United States Patent [19]

Wallace

[11] 4,117,153
[45] Sep. 26, 1978

[54] SUBSTITUTED CARBAMIC ANHYDRIDES

[75] Inventor: Edwin G. Wallace, Orinda, Calif.

[73] Assignee: Stauffer Chemical Company, Westport, Conn.

[21] Appl. No.: 803,089

[22] Filed: Jun. 3, 1977

[51] Int. Cl.$^2$ .................. A01N 9/20; C07C 101/00
[52] U.S. Cl. .................. 424/286; 424/DIG. 8; 260/546
[58] Field of Search .................. 424/286, DIG. 8; 260/546

[56] References Cited

U.S. PATENT DOCUMENTS

| Re. 22,750 | 4/1946 | Tisdale et al. .................. 424/286 |
| 2,610,140 | 9/1952 | Santiuasi .................. 424/286 X |

OTHER PUBLICATIONS

Klopping et al., C. A. vol. 46, 5241f(1952).
Bagdow et al., C.A. vol. 51, 9901f(1957).

*Primary Examiner*—Allen J. Robinson
*Attorney, Agent, or Firm*—Michael J. Bradley

[57] ABSTRACT

Compounds defined by the generic formula

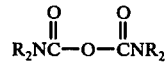

wherein R is $C_1$ to $C_6$ alkyl or when taken together form a single hexamethyl carbon chain are disclosed which are aphicidally effective.

9 Claims, No Drawings

SUBSTITUTED CARBAMIC ANHYDRIDES

BACKGROUND OF THE INVENTION

Prior art of which applicant is aware is Klopping & van der Kirk, Rec. Trav. Chem. 70, 917–39 (1951) reported at Chemical Abstracts 46, 5241g (1952) and Bogdon & Dubois, Arch. intern. pharmacodynamie 108, 27–37 (1956) reported at Chemical Abstracts 51, 9901f which disclose compounds similar to applicant's novel compounds.

BRIEF DESCRIPTION OF THE INVENTION

The present invention relates to a novel class of substituted carbamic anhydride compounds and to their use as aphicides when used in an aphicidally effective amount. In particular, this invention relates to compounds having the formula

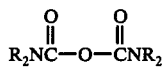

in which R is alkyl containing from 1 to 6 carbon atoms; preferably from 1 to 3, and more preferably from 1 to 2, with methyl being most preferred or when taken together form a single hexamethyl carbon chain.

By "alkyl" is meant a straight- or branched-chain saturated hydrocarbn group containing the indicated number of carbon atoms. Examples of groups conforming to this description are methyl, ethyl, n-propyl, isopropyl, butyl, isobutyl, sec-butyl, pentyl, isopentyl, sec-pentyl, hexyl, isohexyl and sec-hexyl.

All stated ranges of quantities of carbon atoms are intended to be inclusive of their upper and lower limits.

By "aphicidally effective amount" is meant the amount of the herein disclosed aphicidal compounds which when applied in any conventional manner to the habitat of aphids, the feedstuffs of aphids, or the aphids themselves, will kill or substantially injure a significant portion thereof.

DETAILED DESCRIPTION OF THE INVENTION

The compounds of this invention are prepared by the generalized reaction scheme shown below

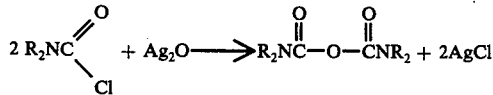

The group R is as defined above. It is preferable to carry out the reaction in a solvent such as benzene or toluene or mixtures thereof at from about −10° C to about 25° C. The reaction product may be filtered to remove solid precipitate with the solid being washed with additional solvent to recover any adsorbed product. The product may then be recovered from the solvent and low boiling by-products by conventional separation techniques such as distillation or vacuum flashing of the solvent and by-products. The starting materials are known and commercially available.

Although, the above reactions will proceed at any temperature, due to the exothermic nature of the reaction, it is preferred to run the reactions at approximately 0° C.

The compounds are particularly effective as Systemic Aphicides where the aphicidal chemicals can be applied to plants or the locus of plants to be protected and the aphicidal chemical is taken up by the plant from the soil or through its foliage. The plant then assimilates the aphicidal chemical and translocates it to the portion of the plant which the aphids ingest thereby an aphicidally effective amount is administered to the aphids.

The following examples serve to illustrate the preparation of the compounds of the invention.

EXAMPLE I

N,N-DIMETHYL CARBAMIC ANHYDRIDE

A solvent solution of 135 milliliters of dry benzene and 15 milliliters of dry toluene was prepared and placed in a 250 milliliter flask. 32.3 grams (0.3 mole) of freshly distilled dimethyl carbamyl chloride was added to the solvent. The reaction solution was protected from the atmosphere by a $CaCl_2$ drying tube on the vent. 51.7 grams (0.18 mole) of dry $Ag_2O$ was then added to the reaction solution over a period of approximately one minute. The mixture was stirred in the ice bath for approximately 8 ½ – 9 days to effect reaction. The mixture was then warmed to 25° C and filtered by suction through a cintered glass filter. The solid was washed in the filter with dry benzene. The total filtrate was then concentrated in vacuo to remove the solvents.

25.1 grams of liquid crude product was recovered. This liquid was subjected to a high vacuum (10μ) to remove low boiling by-products, such as unreacted starting material and substituted urea by-products. The remaining liquid product crystallized but picked up water from the air easily.

The titled product produced was 9 grams for a yield of 37%. Analysis by Mass Spectrophotometer confirmed 100% pure product. The product's structure was confirmed by Nuclear Magnetic Resonance (NMR) analysis. The liquid product had a $n_D^{30}$ of 1.4521. This compound will be referred to as compound 1.

EXAMPLE II

N,N-DIETHYL CARBAMIC ANHYDRIDE

The procedure and equipment was the same as in Example I with the exception that the reactants were 27.1 grams (0.2 mole) diethyl carbamyl chloride and 27.8 grams (0.12 mole) of dry $Ag_2O$.

The titled product produced was 9.9 grams for a yield of 44%. Analysis by Mass Spectrophotometer confirmed 100% pure product. The product's structure was confirmed by Nuclear Magnetic Resonance (NMR) analysis. The liquid product had a $n_D^{30}$ of 1.4513. This compound will be referred to as compound 2.

EXAMPLE III

N,N-DI-n-PROPYL CARBAMIC ANHYDRIDE

The procedure and equipment was the same as in Example I with the exception that the reactants were 32.7 grams (0.2 mole) di-n-propyl carbamyl chloride and 27.8 grams (0.12 mole) of dry $Ag_2O$.

The titled product produced was 12.5 grams for a yield of 44%. Analysis by Mass Spectrophotometer confirmed 90% of pure product. The product's structure was confirmed by Nuclear Magnetic Resonance (NMR) analysis. The liquid product had a $n_D^{30}$ of 1.4541. This compound will be referred to as compound 3.

EXAMPLE IV

N-HEXAMETHYLENE CARBAMIC ANHYDRIDE

The procedure and equipment was the same as in Example I with the exception that the reactants were 32.3 grams (0.2 mole). N-hexamethylene carbamyl chloride and 27.8 grams (0.12 mole) of dry $Ag_2O$.

The titled product produced was 12 grams for a yield of 45%. Analysis by Mass Spectrophotometer confirmed 70% pure product. The product's structure was confirmed by Nuclear Magnetic Resonance (NMR) analysis. The liquid product had a $n_D^{30}$ of 1.5085. This compound will be referred to as compound 4.

Examples of additional compounds of this type which can be prepared by the above method of selection of the proper alkyl carbamic chloride are:
N,N-dibutyl carbamic anhydrides
N,N-dipentyl carbamic anhydrides
N,N-dihexyl carbamic anhydrides

Aphicide Evaluation

A. Direct Spray Assay on Green Peach Aphid [*Myzus persicae* (Sulzer)]

A radish plant (*Rhaphanus sativus*), approximately 2 centimeters tall, is transplanted into sandy loam soil in a 3-inch clay pot and infested with 25-50 green peach aphids of mixed ages. Twenty-four hours later the plant is sprayed, to the point of runoff, with a 50—50 acetone-water solution of the test compound. The treated plant is held in the greenhouse and mortality is recorded after 48 hours. The primary screening level for this test is 0.05% by weight of the test compound in the acetone-water solution.

B. Systemic Assay on Green Peach Aphid [*Myzus persicae* (Sulzer)]

The test compound is diluted in acetone and an aliquot is thoroughly mixed into 500 grams of dry, sandy loam soil. The treated soil is placed in a pint ice cream carton and a radish plant (*Rhaphanus sativus*) approximately 2 centimeters tall is transplanted into the carton. The plant is then infested with approximately 25 green peach aphids of mixed ages and placed in the greenhouse. Five days later mortality is recorded. The primary screening level for this test is 10 ppm by weight of the test compound in the soil.

C. Direct Spray Assay on Black Bean Aphid [*Aphis fabae* (Scop.)]

A nasturtium plant (*Tropaeolum sp.*), approximately 5 centimeters tall, is transplanted into sandy loam soil in a 3-inch clay pot and infested with 25-50 black bean aphids of mixed ages. Twenty-four hours later, the plant is sprayed, to the point of runoff, with a 50—50 acetone-water solution of the test chemical. The treated plant is held in the greenhouse and mortality is recorded after 48 hours. The primary screening level for this test is 0.05% by weight of the test compound in the acetone-water solution.

D. Systemic Assay on Black Bean Aphid [*Aphis fabae* (Scop.)]

The test chemical is diluted in acetone and an aliquot is thoroughly mixed into 500 grams of dry, sandy loam soil. The treated soil is placed in a pint ice cream carton and a nasturtium plant (*Tropaeolum sp.*) approximately 5 centimeters tall is transplanted into the carton. The plant is then infested with approximately 25 black bean aphids of mixed ages and placed in the greenhouse. Five days later mortality is recorded. The primary screening level for this test is 10 ppm by weight of the test compound in the soil.

The primary screening level in each of the above tests was selected for purpose of convenience only and is not to be understood as representing the highest level at which a viable test for aphicidal activity can be conducted. The aphicidal evaluation proceeded as follows.

For a particular aphid, each compound was initially tested at the primary screening level. Those compounds showing greater than 50% kill at this level were then tested at successively lower levels, until the level was found at which approximately 50% kill was achieved. This level is listed as the $LD_{50}$ (50% lethal dose) value in Table I. For those compounds showing approximately 50% kill at the primary screening level, the primary screening level itself is listed as the $LD_{50}$. For those compounds showing less than 50% kill, the number listed is the primary screening level preceded by a ">" (greater than) sign to indicate that a higher level than that reported must be used to achieve 50% kill. Since no tests were run at concentrations higher than the primary screening level, the data as to this latter group is inconclusive with regard to the activity of the compounds of this group at higher concentrations.

TABLE I

| Aphicidal Effectiveness - Approximate $LD_{50}$ Values | | | | |
|---|---|---|---|---|
| | BBA | | GPA | |
| Compound Number | (1) (%) | (2) (ppm) | (1) (%) | (2) (ppm) |
| 1 | .0005 | .1 | .0005 | .2 |
| 2 | .002 | .8 | .005 | 5 |
| 3 | .03 | >10 | .05 | 10 |
| 4 | .03 | >10 | >.05 | >10 |

BBA: black bean aphid - (1) direct spray, (2) systemic
GPA: green peach aphid - (1) direct spray, (2) systemic
>: "greater than" - indicates compound did not pass primary screen The compounds of this invention are generally used in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water, emulsifying agents; surface active agents, talc; pyrophyllite; diatomite; gypsum; clays; and propellants, such as dichlorodifluoromethane.

The active compounds can further be combined with dust carriers for application as dusts, with granular carriers for application by fertilizer spreaders or ground or airplane seeders, with wettable powders or flowable carriers for application as water suspensions, or with solvents and surface active materials for application as sprays, aerosols, or emulsions. The compounds or their formulated mixtures can be applied to any habitat of the aphid pests. Examples of such habitats are aphid dwellings, clothing, plant surfaces, and soil. If desired, however, the active compositions can be applied directly to organic matter, seeds, or feedstuffs in general, upon which the pests feed, or directly to the pests themselves. When applied in such a manner, it will be advantageous to use a formulation which is not volatile.

The amount of active compound or formulation which is considered to be aphicidally effective is that amount which, when applied to the aphid pest habitat or feedstuff, will kill or substantially injury a significant portion residing or feeding thereon. The active compounds of this invention can be employed either as the sole aphid pesticide component of the formulation or as one of a mixture of compounds in the formulation having similar utility. Furthermore, the presently disclosed aphid pesticide compositions need not be active as such. The purpose of this invention will be fully served by a composition which is rendered active by external influences, such as light, or by physiological action occurring when the preparation is ingested or penetrates into the body of the aphid pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the aphid pesticide composition will comprise not more than about 50.0% by weight of the formulation.

What is claimed is:

1. A compound having the formula

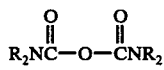

wherein R is alkyl containing from 1 to 2 carbon atoms.

2. The compound of claim 1 wherein R is —CH$_3$.
3. The compound of claim 1 wherein R is —C$_2$H$_5$.
4. A method of controlling aphids comprising applying to said aphids, the habitat or feedstuff of said aphids an aphicidally effective amount of a compound having the formula

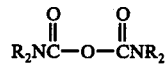

wherein R is alkyl containing from 1 to 2 carbon atoms.

5. The method of claim 4 wherein R is —CH$_3$.
6. The method of claim 4 wherein R is —C$_2$H$_5$.
7. An aphicidal composition comprising:
   1. an aphicidally effective amount of a compound having the formula

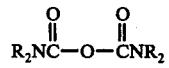

wherein R is alkyl containing from 1 to 2 carbon atoms; and
   2. an inert diluent carrier.
8. The composition of claim 7 wherein R is —CH$_3$.
9. The composition of claim 7 wherein R is —C$_2$H$_5$.